United States Patent [19]

Karkar et al.

[11] Patent Number: 5,249,584
[45] Date of Patent: Oct. 5, 1993

[54] SYRINGE FOR HEMATOCRIT AND OXYGEN SATURATION BLOOD ANALYZER

[76] Inventors: Maurice N. Karkar, 26842 Calle Maria, Mission Viejo, Calif. 92692; James C. Velnosky, 6014 Amethyst Ave., Alta Loma, Calif. 91701

[21] Appl. No.: 789,088

[22] Filed: Nov. 7, 1991

Related U.S. Application Data

[62] Division of Ser. No. 526,184, May 18, 1990, Pat. No. 5,066,859.

[51] Int. Cl.$^5$ ............................................. A61B 5/00
[52] U.S. Cl. ................................. 128/765; 604/187; 604/218; 356/39; 356/246; 128/771
[58] Field of Search ............... 604/187, 218, 232; 356/246, 39; 128/703, 765, 771

[56] References Cited

U.S. PATENT DOCUMENTS

| | | | |
|---|---|---|---|
| Re. 30,391 | 9/1980 | Liston | 356/409 |
| 3,732,079 | 5/1973 | Davis | 128/771 X |
| 3,860,347 | 1/1975 | Jones | 356/246 |
| 3,869,215 | 3/1975 | Nolan | 356/246 |
| 3,942,514 | 3/1976 | Ogle | 128/771 X |
| 3,961,899 | 6/1976 | Trivedi et al. | 356/246 X |
| 3,999,948 | 12/1976 | Deindoerfer et al. | 356/246 X |
| 4,060,073 | 11/1977 | Collica et al. | 604/187 X |
| 4,062,353 | 12/1977 | Foster et al. | 604/187 X |
| 4,178,071 | 12/1979 | Asbell | 604/187 X |
| 4,304,488 | 12/1981 | Asakura et al. | 356/39 |
| 4,333,456 | 6/1982 | Webb | 604/232 X |
| 4,420,254 | 12/1983 | Smeaton | 356/246 |
| 4,444,498 | 4/1984 | Heinemann | 356/246 |
| 4,447,150 | 5/1985 | Heinemann | 356/41 |
| 4,576,477 | 3/1986 | Corbal et al. | 604/39 |
| 4,675,019 | 6/1987 | Bellhouse et al. | 604/408 |
| 4,745,279 | 5/1988 | Karkar et al. | 250/343 |
| 4,776,340 | 10/1988 | Moran et al. | 128/634 |
| 4,931,040 | 6/1990 | Haber et al. | 604/110 |
| 5,066,859 | 11/1991 | Karkar et al. | 250/339 |

FOREIGN PATENT DOCUMENTS 0085355  5/1985  Japan .................. 356/246

OTHER PUBLICATIONS

An article from IEEE Transactions on Biomedical Engineering, "A Miniature Hybrid Reflection Type Optical Sensor for Measurement of Hemoglobin Content and Oxygen Saturation of Whole Blood", Mar. 1988.
An article from IEEE Transactions on Biomedical Engineering, "Role of Light Scattering in Whole Blood Oximetry", Mar. 1986.
An article from Medical & Biological Engineering & Computing, "Back-Scattering of Light by Red Cell Suspensions", 1979 issue.

Primary Examiner—C. Fred Rosenbaum
Assistant Examiner—Mark O. Polutta
Attorney, Agent, or Firm—Stetina & Brunda

[57] ABSTRACT

An improved blood analyzing device is disclosed for measuring the hematocrit and oxygen saturation levels of a quantity of blood. The device is a syringe containing a single optical window insert into the tubular barrel.

10 Claims, 4 Drawing Sheets

FIG. 7  OXYGEN SATURATION SENSITIVITY

| OXYGEN SATURATION (%) | RATIO OF SIGNALS (VOLTS) RED/INFRARED |
|---|---|
| 95 | 2.0 |
| 85 | 1.4 |
| 76 | 1.0 |
| 55 | .70 |
| 40 | .55 |

FIG. 8  HEMATOCRIT SENSITIVITY

| HEMATOCRIT (%) | SIGNAL (VOLTS) |
|---|---|
| 45 | .80 |
| 40 | .87 |
| 35 | .95 |
| 30 | 1.15 |
| 25 | 1.40 |
| 20 | 1.60 |

FIG. 9  COMPENSATION OF OXYGEN SATURATION WITH HEMATOCRIT

| | HEMATOCRIT (%) | | |
|---|---|---|---|
| | 45 | 30 | 20 |
| OXYGEN SATURATION (%) | 95 | 93 | 91 |
| | 70 | 70 | 70 |
| | 95 | 97 | 99 |

FIG. 10  COMPENSATION OF HEMATOCRIT WITH OXYGEN SATURATION

| | OXYGEN SATURATION (%) | | | | |
|---|---|---|---|---|---|
| | 100 | 95 | 80 | 70 | 50 |
| HEMATOCRIT | 46 | 43 | 42.7 | 42.3 | 42.3 |
| (%) | 21.8 | 21.8 | 22.0 | 21.8 | 21.8 |

FIG. 11  EFFECTS OF pH ON OXYGEN SATURATION

| | pH | | | | |
|---|---|---|---|---|---|
| | 7.0 | 7.2 | 7.4 | 7.6 | 7.8 |
| OXYGEN SATURATION (%) | 90.8 | 90.4 | 90 | 89.5 | 89.0 |

FIG. 12  EFFECTS OF pH ON HEMATOCRIT

| | pH | | | | |
|---|---|---|---|---|---|
| | 7.8 | 7.6 | 7.4 | 7.2 | 7.0 |
| HEMATOCRIT (%) | 47 | 46 | 45 | 44 | 43 |
| | 31 | 30.5 | 30 | 29.5 | 29 |
| | 20.4 | 20.2 | 20 | 19.8 | 19.7 |

SYRINGE FOR HEMATOCRIT AND OXYGEN SATURATION BLOOD ANALYZER

This application is a division of application Ser. No. 07/526,184, filed May 18, 1990 now U.S. Pat. No. 5,066,859.

FIELD OF THE INVENTION

The present invention relates generally to systems used for measuring properties of materials in suspension in fluids, and more particularly to a portable apparatus for measuring hematocrit and oxygen saturation levels of a quantity of blood.

BACKGROUND OF THE INVENTION

As is well known in the medical profession, both the hematocrit and oxygen saturation levels of blood can he measured optically. Oftentimes, such information is of vital importance for the proper medical treatment of an individual. Examples of devices for performing such measurements are shown in U.S. Pat. No. 4,447,150 to Heinemann, which discloses an apparatus and method for measuring blood oxygen saturation and U.S. Pat. No. 4,745,279 to Karkar et al., which discloses a hematocrit measuring apparatus.

In these devices and others used to perform such operations, the oxygen saturation level and the hematocrit level are obtained by measuring the amount of scattering of light of various wavelengths which occurs within a quantity of blood. Thus, as can be appreciated, it is particularly important that the light source used to infuse the various wavelengths of light into the blood be such that it provide a uniform distribution of such light so as to facilitate accurate scattering effects within the blood. Also, with regard to both oxygen saturation and hematocrit measurements, the accuracy of these measurements is further affected by the presence of proteins and the pH level of the blood. Moreover, in measuring hematocrit there is an effect on the measurement attributable to the oxygen saturation level, while in measuring oxygen saturation, there is an effect on the measurement attributable to the hematocrit level; i.e. oxygen saturation level and hematocrit level of a blood sample are interelated.

As is well known, the use of optical fibers generally provides a light source having the advantage that light is emitted from such fibers at a more uniform distribution than that emitted from conventionally-known light emitting diodes (LED's). In the hematocrit measuring device disclosed in Karkar et al., LED's are used as a means of infusing light into the blood. Thus, though this device provides a generally reliable measuring means, the hematocrit measurement obtained by this device is more prone to inaccuracy due to the utilization of LED's as a light source. Also, though this prior art device provides a hematocrit measurement which is compensated for the effects of oxygen saturation, it does not provide a separate oxygen saturation measurement compensated for the effects of hematocrit, nor does it possess the capacity to compensate the hematocrit measurement for the effects of proteins and pH. Though the Heinemann 4,447,150 patent contemplates the use of fiber optics in coupling light to a quantity of blood, the device disclosed by this reference provides only an oxygen saturation measurement which is compensated for the effects of hematocrit, but not for the effects of proteins and pH. Additionally, the device taught by this particular reference is adapted to obtain an oxygen saturation measurement only from blood in a flowing mode and not from a quantity of blood in a static mode, i.e. environment. A device utilizing fiber optics for obtaining hematocrit and oxygen saturation measurements of blood is also disclosed in U.S. Pat. No. 4,776,340 to Moran et al. Though this device provides both an independent hematocrit measurement and an oxygen saturation measurement that is compensated for hematocrit, it does not provide a hematocrit measurement which is compensated for oxygen saturation, nor does it compensate either measurement for the effects of proteins and pH. More importantly, this particular reference discloses a catheter used in the critical care environment of a hospital. In this regard, utilization of this device involves the direct insertion of an optical fiber into the bloodstream of a patient, i.e. in situ application, thus limiting use of the device to blood in a flowing mode environment. Additionally, because the optical fiber comes into direct contact with the blood of the patient, the fiber must be replaced after each application and the measuring device re-calibrated for each use of a new catheter/optical fiber.

With respect to the Heinemann and Moran references, the importance of being able to obtain hematocrit and oxygen saturation measurements from blood in a static rather than a flowing mode, wherein blood is drawn into a syringe or cuvette and tested while therein, achieves added significance when one considers the risks associated with handling blood, particularly due to the current AIDs epidemic. Though Karkar et al. contemplates testing blood in a static mode, no consideration is given for the settling of red blood cells in the blood containment vessel which could also adversely effect hematocrit and oxygen saturation measurements.

Other hematocrit and oxygen saturation measuring devices known in the art also include many of the aforementioned shortcomings. Additionally, many of these devices are extremely costly and difficult to utilize. Thus, there exists a need in the art for a cost efficient measuring device providing a hematocrit measurement of increased accuracy which is compensated for the effects of oxygen saturation, pH, and proteins, and additionally provides an oxygen saturation measurement of increased accuracy which is compensated for the effects of hematocrit, pH, and proteins. Moreover, there exists a need for an analytical measuring device which can obtain such measurements from a quantity of blood wherein the blood may be tested in a static mode while being maintained within the interior of a containment apparatus such that a minimal amount of direct contact with the blood need be undertaken, and further wherein red blood cells within the quantity of blood being tested in a static mode are prevented from settling in the containment apparatus.

SUMMARY OF THE INVENTION

In accordance with the preferred embodiment of the present invention, there is provided an improved apparatus and method for measuring the hematocrit and oxygen saturation levels of a quantity of blood. In the preferred embodiment the device generally comprises a housing having a key pad and display panel contained on the outer surface thereof Attached to the housing is a carriage into which a syringe containing a quantity of blood is placed. The syringe which is utilized includes a window adapted to receive and reflect back light transmissions of various wavelengths. Disposed within the carriage are a fiber optic light source and multiple fiber optic, light sensitive detectors. The light source is preferably comprised of two light diodes (LED's), wherein one is adapted to emit light at a first known wavelength, i.e. preferably 660 nanometer red wavelength and the other adapted to emit light at a second known wavelength, i.e. preferably 805 nanometer infrared wavelength. Through the utilization of an optical splitter, the light outputs from each of the LED's are merged into a single light emission path, such that light from either of both wavelengths will exit from a single optical fiber. Importantly, during a testing process, each of the LED's are turned on alternately, whereby the two distinct wavelengths of light are emitted through the emission path into the blood in a reasonably uniform pattern. A second optical fiber is placed at a specific distance separation from the light emitting fiber and is adapted to receive light at the 805 nanometer wavelength after such light has been scattered by the blood, to provide a hematocrit measurement. A third fiber is placed at the same specific distance separation from the light emitting fiber as the second fiber and is used as a parity fiber for the second fiber. In this respect, the hematocrit measurement signal received from the third fiber is compared to the signal received by the second fiber. Differences in the signals obtained by the second and third fibers are used to indicate if the surfaces of these fibers are damaged or covered with particular matter, such as dust, and provide a suitable warning to the device user.

Fourth and fifth optical fibers are additionally placed at symetric, specific separations from the light emitting fiber, with the fourth fiber being adapted to receive light at both the 660 and 805 nanometer wavelengths to obtain a measurement of oxygen saturation in the blood. The fifth fiber also acts as a parity fiber for the oxygen saturation measurement process. As with the second and third fibers, signals from both the fourth and fifth fibers are compared to provide a check on the condition of the fourth and fifth fiber surfaces and provide appropriate warnings.

Importantly, before the aforementioned measuring processes take place, light from the emitting fiber is checked by a sixth and seventh fiber also disposed at symetrical specific separations from the light emitting fiber. In this respect, light from both wavelengths is transmitted through the air before placing a syringe containing blood within the carriage, wherein the intensity is received and measured by the sixth fiber. This measurement is then compared to a previously set level in the memory of the device as a means of checking the light output from the emission fiber and the calibration of the device. The seventh fiber is used as a parity fiber wherein a similar technique to that previously set forth with regard to the hematocrit and oxygen saturation detection fibers is used for checking the operation of the sixth fiber. The specific separations of all the receiving fibers disposed within the carriage with respect to the light emission fiber are selected to give optimal measurement sensitivities based on non-differential geometry.

The carriage of the device further includes a blood mixing mechanism to prevent red blood cells from settling at the bottom of the syringe, thus adversely affecting the hematocrit and oxygen saturation measurements taken by the optical channels of the device. The carriage also includes an electromagnetic flux system designed to migrate protein away from the optical channels to reduce the adverse effects that protein has on the optical technology during a measurement procedure.

The signals received from the multiple optical fibers of the present invention are amplified and buffered within an optical interface module. These analog signals, after being filtered and converted into digital signals, are then further processed to obtain final values of hematocrit and oxygen saturation. Importantly, the output measurement of hematocrit is compensated for the effects of oxygen saturation, pH, and temperature, while the output measurement of oxygen saturation is compensated for the effects of hematocrit, pH, and temperature. The pH and temperature values utilized in the compensation process are entered through the keypad contained on the exterior surface of the housing.

The syringe used in conjunction with the present invention is specifically adapted for obtaining the hematocrit and oxygen saturation measurements. In this regard, the syringe is constructed to include a window disposed within the tubular portion thereof. Importantly, the window is positioned on the syringe such that when the syringe is placed into the carriage, the window will be vertically aligned with the light emitting fiber as well as the hematocrit and oxygen saturation detection fibers. The window is fabricated from a material which provides a reasonably clear, repeatable optical path for the light emitted from the light emitting fiber.

It is an object of the present invention to provide an apparatus for measuring the hematocrit and oxygen saturation levels of a quantity of blood in either a static or flowing mode environment, based on the scattering within the blood of light emitted from a fiber optic source of known multiple wavelengths.

Another object of the present invention is to provide an apparatus for measuring the hematocrit and oxygen saturation levels of a quantity of blood wherein the measurement of hematocrit is compensated for effects attributable to oxygen saturation, temperature, and pH and the measurement of oxygen saturation is compensated for effects attributable to hematocrit, temperature, and pH.

Another object of the present invention is to provide an apparatus for measuring the hematocrit and oxygen saturation levels of a quantity of blood adapted to decrease the amount of handling of the blood which is required to obtain such measurements.

A further object of the present invention is to provide an apparatus for measuring the hematocrit and oxygen saturation levels of a quantity of blood wherein the apparatus includes a magnetizing assembly operable to separate protein layers from red blood cells in order to minimize the effects of proteins on the hematocrit and oxygen saturation measurements.

A still further object of the present invention is to provide an apparatus for measuring the hematocrit and oxygen saturation levels of a quantity of blood incorporating a mixing mechanism used to prevent red blood cells from settling in a portion of a blood containment receptacle.

Further objects and advantages of the invention will become apparent to those skilled in the art upon reading and consideration of the following description of a preferred embodiment and the accompanying drawings.

BRIEF DESCRIPTION OF THE DRAWINGS

These as well as other features of the present invention will become apparent upon reference to the drawings wherein.

DETAILED DESCRIPTION OF THE PREFERRED EMBODIMENT

Figures 1, 2, 3:
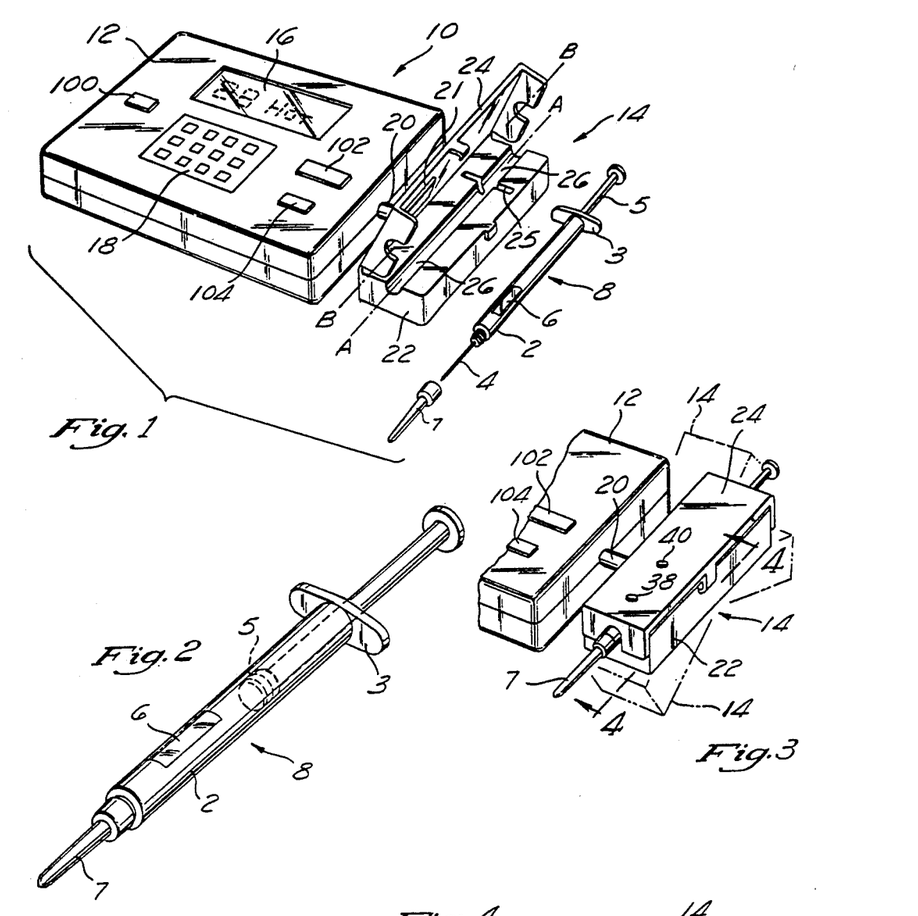
FIG. 1 is a perspective view of the measuring device of the present invention illustrating the housing, carriage, and a syringe specifically adapted for utilization in the present invention.
FIG. 2 is a perspective view of the syringe shown in FIG. 1 further defining the syringe features.
FIG. 3 is a perspective view of the carriage component of the measuring device including the syringe therein, as positioned during the measuring mode, further illustrating the relative oscillatory positions of the carriage during a blood mixing and measuring operation.

Referring now to the drawings wherein the showings are for purposes of illustrating a preferred embodiment of the present invention only and not for the purposes of limiting the same, FIG. 1 perspectively illustrates the hematocrit and oxygen saturation measuring device 10 of the present invention. It will be appreciated by those skilled in the art that measuring device 10, as fully described in the following paragraphs, may also be utilized for measuring other properties of blood in addition to hematocrit and oxygen saturation such as the presence of glucose or electrolytes. Measuring device 10 generally comprises a housing 12 and a carriage 14 which is preferably although not necessarily connected thereto. Included on the outer surface of housing 12 is a display panel 16 which is used to provide a user with a digital and alpha-numeric readout corresponding to both a hematocrit measurement and an oxygen saturation measurement as well as a visual readout of data manually input into the device 10. Also included on the outer surface of housing 12 is a keypad 18 which is used to input various information into device 10 as will be explained in greater detail infra. Disposed within housing 12 are the various electrical components (schematically illustrated in FIG. 6) which are used to carry out the various motor control and signal processing functions required for the proper operation of device 10 as will also be explained in greater detail infra. In the preferred embodiment of the present invention, the measurement process is conducted through the placement of a specially adapted syringe 8 containing a quantity of blood therein into carriage 14.

BLOOD MIXING AND MAGNETIZING SYSTEMS

Carriage 14 is preferably attached to one side of housing 12 via a common mechanical and electrical connection. In the preferred embodiment of the present invention, a shaft 20 is used to rigidly attach carriage 14 to housing 12. Importantly, shaft 20 is an integral component of a mixing mechanism included as a component of measuring device 10. In this respect, a motor 60 (schematically illustrated in FIG. 6) is disposed within housing 12. The end of shaft 20 extending into housing 12, as best seen in FIG. 3, is connected to motor 60, with the opposing end of shaft 20 being connected to carriage 14. Motor 60 is operative to oscillate carriage 14 back and forth in a rooking motion about the axis of shaft 20, as illustrated in phantom lines in FIG. 3. In the preferred embodiment, such oscillation occurs at approximately 60 cycles per minute which has been found to prevent red blood cells in a blood sample from settling in a portion of syringe 8, thereby increasing the accuracy of the hematocrit and oxygen saturation measurements. It will be appreciated that any of a variety of methods may be utilized to accomplish the blood mixing or agitation process, including an ultrasound emitter mounted to carriage 14, wherein sound waves from the emitter are directed toward syringe 8. Such a blood mixing operation is generally only required when measuring processes are conducted with blood in a static mode (i.e. within a syringe). Thus, when blood is tested in the flowing mode, i.e. through flow environment, an alternative embodiment of the present invention is contemplated wherein device 10 is constructed such that carriage 14 may be placed remote from housing 12, thus being connected to housing 12 only by means of an electrical connection such as a cable, and not by shaft 20. Such a particular arrangement allows carriage 14 to be interfaced to a syringe-shaped blood containment vessel or cuvette which is placed in an oxygenator line in a procedure such as open-heart surgery. Carriage 14 further preferably includes a magnetizing device 21 disposed adjacent a portion thereof. Magnetizing device 21 is operative to subject the quantity of blood contained within syringe 8 to magnetic effects, thereby separating protein layers from red blood cells so as to enhance the accuracy of the hematocrit and oxygen saturation measurements. Carriage 14 is also adapted to be interchangeably connected to housing 12 so that carriages accommodating syringes or containment vessels of varying sizes may be utilized. In this regard, one carriage 14 may be adapted to receive a 1 cc syringe while another is adapted to receive a 3 cc syringe.

CARRIAGE CONFIGURATION AND SENSOR ARRAY

Figure 4:
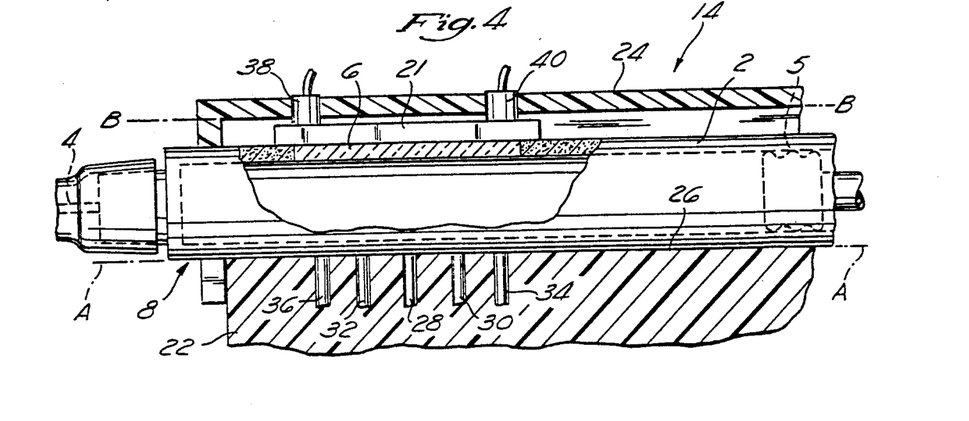
FIG. 4 is a cross-sectional view of the carriage component showing the engagement of the syringe therein, taken along line 4—4 of FIG. 3.

Carriage 14 generally comprises an elongate, horizontally-disposed lower member 22 and an elongate, horizontally-disposed upper member 24 cooperatively and preferably pivotally engaged thereto. Importantly, upper member 24 is attached to lower member 22 so as to be movable between a first open position as shown in FIG. 1 and a second closed position as shown in FIG. 3. Lower member 22 includes a longitudinally extending recess portion 26 which defines a first longitudinal axis A—A on an interior surface thereof. In the preferred embodiment, recess portion 26 is sized and configured in a complementary configuration to receive syringe 8. The bottom surface of upper member 24 further defines a second longitudinally extending axis B—B. Referring now to FIG. 4, a light emitting optical fiber 28 is disposed within recess portion 26 of lower member 22 at a desired point on axis A—A. A first oxygen saturation detection optical fiber 30 and a second oxygen saturation detection fiber 32 are disposed at locations along first axis A—A on opposite sides of and preferably equal distances from light emitting fiber 28. A first hematocrit detection fiber 34 and a second hematocrit detection optical fiber 36 are also disposed at locations along first axis A—A on opposite sides of and preferably equal distances from light emitting fiber 28 and equal distances from first oxygen saturation fiber 30 and second oxygen saturation fiber 32, such that first oxygen saturation fiber 30 is disposed between light emitting fiber 28 and first hematocrit detection fiber 34 with second oxygen saturation fiber 32 being disposed between light emitting fiber 28 and second hematocrit detection fiber 36. Disposed at locations along second axis B—B of upper member 24 are a first calibration optical fiber 38 and second calibration optical fiber 40. Importantly, second axis B—B is disposed on upper member 24 such that when upper member 24 is in a closed position, second axis B—B is preferably vertically aligned with and parallel to first axis A—A. First calibration fiber 38 and second calibration fiber 40 are disposed on axis B-B such that when upper member 24 is in the closed position, first calibration fiber 38 is positioned at a point one-half the distance between light emitting fiber 28 and first hematocrit detection fiber 34, and second calibration fiber 40 is positioned at a distance one-half the distance between light emitting fiber 28 and second hematocrit detection fiber 36. Also disposed adjacent second axis B—B is magnetizing device 21.

It should be noted that the geometrical configuration of light emitting fiber 28 in relation to hematocrit detection fibers 34, 36 and oxygen saturation detection fibers 30, 32 is extremely critical in determining the sensitivities of the hematocrit and oxygen saturation measurements. These sensitivities are dependent upon such factors as the diameters of the optical fibers, the distal separations between the optical fibers, the depth of the optical interface between the optical fibers and the blood being tested, the numerical aperture of the optical fibers, the pattern of radiation of the light exiting the light emitting fiber 28, and the angular positioning of the optical fibers with respect to the optical interface between the fibers and the blood. In this regard, variations in these parameters will introduce variations in the sensitivities of the hematocrit and oxygen saturation measurements, as well as the calibration of measuring device 10. It has been experimentally determined that the region of a quantity of blood immediately adjacent a light emitting fiber is a near field absorption dependent region and is therefore well suited for obtaining oxygen saturation measurements of the blood. It has also been determined that the region of a quantity of blood distant from a light emitting fiber is a far field light scattering region and is therefore well suited for obtaining hematocrit measurements of the blood. In the present invention the geometric configurations of all the optical fibers are selected to give optimal sensitivities. In the preferred embodiment, light emitting fiber 28 and detection fibers 30, 32, 34, and 36 have a 1 millimeter diameter. Additionally, oxygen saturation detection fibers 30, 32 are each spaced 1.1 millimeters from light emitting fiber 28 in the orientation previously specified, wherein fibers 30, 32 are disposed on opposite sides of fiber 28 along axis A—A. Hematocrit detection fibers 34, 36 are each spaced 3.3 millimeters from light emitting fiber 28 and are also oriented as previously specified wherein fibers 34, 36 are also disposed on opposite sides of fiber 28 along axis A—A.

The top surfaces of all the optical fibers exposed to syringe 8 during a measurement procedure are preferably coated with a clear elastomer which can be easily cleaned or replaced if damaged. Such cleaning of the surfaces is preferably accomplished by placing a piece of scotch tape on the top surface and removing it, though it will be appreciated that other conventional cleaning procedures may be utilized.

SENSOR OPERATION

Figure 5:
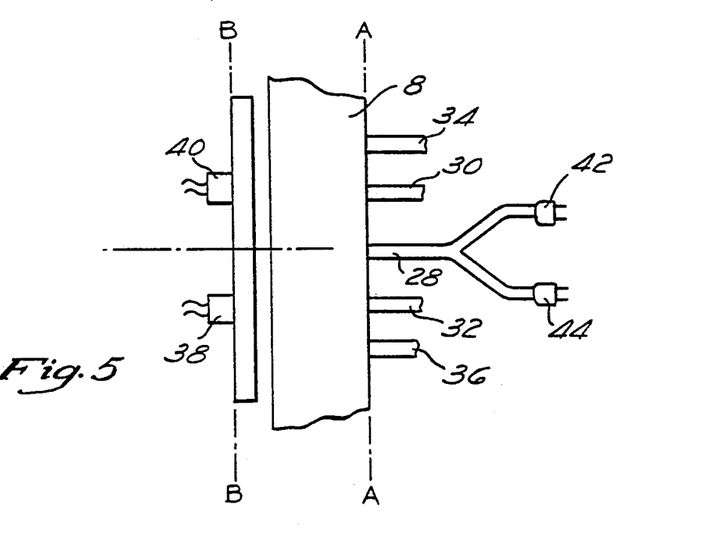
FIG. 5 is a schematic view of the carriage component further illustrating the light emitting diode and optical sensor physical configuration of the present invention.

Referring now to FIG. 5, light emitting fiber 28, through the utilization of a conventional optical splitter, transmits light emanating from both a first light emitting diode 42 and a second light emitting diode 44. First diode is adapted to emit light at a first selected wavelength, preferably 805 nanometer infrared wavelength, while second diode 44 is adapted to emit light at a second selected wavelength, preferably 660 nanometer red wavelength. Such specific selected wavelengths are chosen dependent upon measurement parameters for the measurement device 10 and may be varied at manufacture of the device as desired. During operation of device 10, diode 42 and diode 44 are driven by electronic current drivers, multiplexed in time, thereby turning on diode 42 and diode 44 alternately, whereby both specifically known wavelengths of light are separately emitted through light emitting fiber 28 into the blood contained within syringe 8. It will be appreciated that any light source can be utilized as an alternative to the LED's, one such alternative being incandescent light with filters at the 660-nanometer and 805-nanometer wavelengths. Additionally, the light channels, as an alternative to being fiber optic, can be comprised of light rods with or without lenses on their tips. It is further contemplated that two distinct light emission paths may be utilized, wherein each provides a specific wavelength of light and is positioned along first axis A—A so as to provide a non-differential geometric relationship between the hematocrit and oxygen saturation detection fibers. Infrared light emitted from first diode 42 is directed into and subsequently scattered, i.e. diffused, by the blood within syringe 8. First hematocrit detection fiber detects such light after the scattering thereof and generates a first hematocrit voltage signal HCT1. Second hematocrit detection fiber 36 likewise detects light emanating from diode 42 which is scattered by the blood and generates a second hematocrit signal HCT2. Importantly, fiber 36 is used as a parity fiber for fiber 34, wherein HCT2 is compared to HCT1. In this regard, HCT2 is used to compensate HCT1 for non-uniform light emission properties of the blood and imperfections in the syringe attributable to manufacturing tolerances, dirt, or optical clarity of the syringe wall. Further, a comparison of HCT1 and HCT2 provides an indication as to whether fiber 34 or fiber 36 is damaged or covered with particulate matter. In situations where any of the aforementioned problems are encountered, system architecture activates an appropriate warning signal via control electronics discussed infra to alert the user of device 10 to an error condition during the measurement process.

Scattered light originating from diode 42 is also received by first oxygen saturation detection fiber 30 which in turn generates a first oxygen saturation signal SAT1. Second oxygen saturation detection fiber 32 also receives the scattered light originating from diode 42 and subsequently generates a second oxygen saturation signal SAT2. In this regard, fiber 32 is used as a parity fiber for fiber 30, wherein SAT2 is compared to SAT1 for the same purposes as disclosed previously with respect to hematocrit detection fibers 34,36. After this particular process has been completed, light emitting fiber 28 then transmits light emanating from second light emitting diode 44, which is also directed into and subsequently scattered by the blood contained within syringe 8. First oxygen saturation detection fiber 30 detects this light and generates a third oxygen saturation signal SAT3. During this process, second oxygen saturation detection fiber 32 once again acts as a parity fiber, thereby generating a fourth oxygen saturation signal SAT4 which is compared to SAT3 for the same reasons as discussed previously. Importantly, the actual oxygen saturation level of the blood is obtained by computing a ratio between compensated SAT1 and SAT3 signals, while the actual hematocrit level of the blood is attained by only a compensated SAT1 signal. A more detailed explanation of the empirical relationship of the hematocrit signal and oxygen saturation signal values is disclosed in U.S. Pat. Nos. 4,745,279, issued to Karkar et al. and U.S. Pat. No. 4,444,498 issued to Heinemann, the disclosures of which are expressly incorporated herein by reference.

Before a hematocrit and oxygen saturation testing process occurs, as part of a calibration procedure, light from both wavelengths is independently and sequentially transmitted from light emitting fiber 28 through recessed portion 26 of carriage 14, before syringe 8 is placed thereinto. Importantly, upper member 24 must be in a closed position when the calibration process is conducted. The emitted light is detected by first calibration fiber 38 which is disposed on second axis B—B as previously set forth. First calibration fiber 38 receives the unscattered light, and generates a first calibration signal CT1. Second calibration fiber 40, which also serves as a parity fiber, likewise receives the unscattered light and generates a second calibration signal CT2. CT2 is then compared to CT1 to determine the uniformity of light emissions from light emitting fiber 28 and the clarity of the surface of first calibration fiber 40. The compensated CT1 signal is then compared to a previously set level in the memory 58 of device 10, thereby checking for a proper light output from light emitting fiber 28 as a means of assuring proper calibration of device 10. Hematocrit detection fibers 34, 36, and oxygen saturation detection fibers 30, 32 are also activated during the calibration process to monitor for a proper angle of emission from light emitting fiber 28. In this respect, these detection fibers will also have the capacity to generate compensation constants which will be stored into the memory 58 of device 10 or provide a warning to the operator of a defect which is beyond calibration parameters.

In the preferred embodiment, the compensation/calibration process is preferably conducted by the application of the following sequence of steps:

CT1/CT2=X

CT2/CT1=Y

If SAT2/SAT1=Y—fibers okay.

If SAT2/SAT1 does not equal Y—clean or repair fibers.

If SAT1/SAT2=X—fibers okay.

If SAT1/SAT2 does not equal X—clean or repair fibers (same process conducted with SAT3 and SAT4).

If HCT2/HCT1>X—clean or repair fibers.

If any signal is greater or less than the previously set compensation level by 10%—olean or repair fibers.

First calibration fiber 38 and second calibration fiber 40 are also activated a second time during the hematocrit and oxygen saturation testing procedure. In this regard, first calibration fiber 38 and second calibration fiber 40 are operable to provide further compensation for non-uniformity of light emissions from light emitting fiber 28, or inhomogenity of the medium as would be produced by the presence of bubbles in the blood since each would receive equal light if the blood disposed within syringe 8 allowed the particular light emissions to pass through in a perfectly uniform manner. Any such lack of uniformity in the syringe optical surface is detected by calibration fibers 38,40 and the effects removed from the compensated hematocrit and oxygen saturation signals.

It will be appreciated that various numbers and combinations of hematocrit, oxygen saturation, and calibration fibers, i.e. sensors, may be utilized to achieve the aforementioned results, and that the configurations of such fibers as set forth herein is intended to address only the preferred embodiment of the present invention.

SIGNAL PROCESSING

Figure 6:
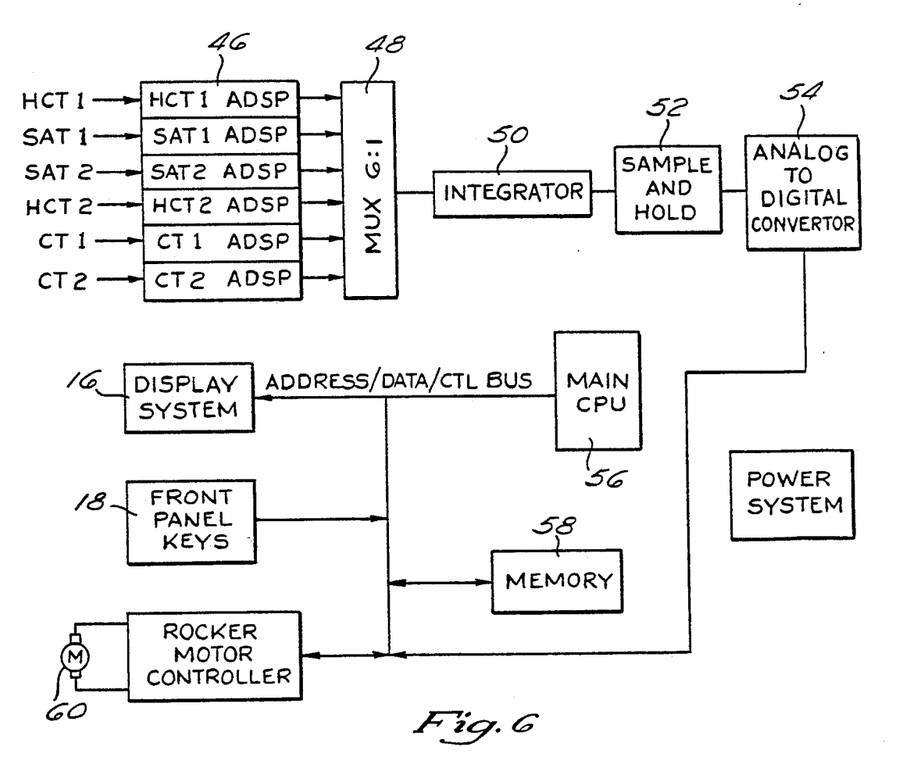
FIG. 6 is an electrical schematic illustrating the signal processing system utilized in conjunction with the present invention.

FIG. 6 illustrates schematically the signal processing and control electronics utilized in the present invention. The HCT1, HCT2, SAT1, SAT2, CT1, and CT2 signals generated by reception of light by the plural optical sensors are amplified and buffered within an optical interface module 46 to allow carriage 14 to be remote from housing 12 in cases when measurements of blood are taken in a flow-through mode wherein the blood containment vessel is remotely disposed from housing 12. The amplified signals are further amplified in accordance with the range of expected light detection signal strengths. The signals are then filtered within optical interface module 46 commensurate with system noise parameters, and outside interference such as room light and 60 Hertz transmissions in surrounding power lines. These signals are then transferred to a multiplexer 48. The signal values are then integrated into a fixed slice in time by integrator 50 and latched into a sample and hold circuit 52 for convertion into digital-numerical values through an analog-to-digital converter 54. The digitally converted values are then processed by the main CPU 56, wherein main CPU 56 further filters the signals for physiological interference when device 10 is being utilized with blood in a flow-through operational mode, or for motor rotation when device 10 is being utilized with blood in a static mode contained within syringe 8. Examples of such physiological interference are a blood pump when in use, the beating heart of a patient and other cyclic effects of the human body, or effects attributable to man-made attached devices. With respect to the effects of motor operation, the motor disposed within housing 12 used to cyclically oscillate or rock the carriage and thereby maintain the fluid suspension within syringe 8 affects the signals in a synchronous cylic manner and thus just also be filtered via conventional filtering techniques to achieve accurate measurements. After such filtering, the signals are then converted to the final values of hematocrit and oxygen saturation. Importantly, the measurement of hematocrit is compensated for the effects of oxygen saturation, while the measurement of oxygen saturation is compensated for the effects of hematocrit. Additionally, the measurements of hematocrit and oxygen saturation are also compensated for the effects of pH and temperature. Both the pH and temperature values may be entered by the user through the utilization of keypad 18 on housing 12 before the actual test procedure begins. The approach used to compensate the hematocrit and oxygen saturation measurements for pH, temperature, and the effects of each on the other, is through the use of tables which are derived from empirical data obtained from presently known experimental techniques and stored within memory module 58. Referring now to FIGS. 7-12, examples of such tables are shown wherein each contains a limited sampling of values, included here only for purposes of explaining the following sequence of steps used to obtain the compensated hematocrit and oxygen saturation measurements in the preferred embodiment.

Figure 7:
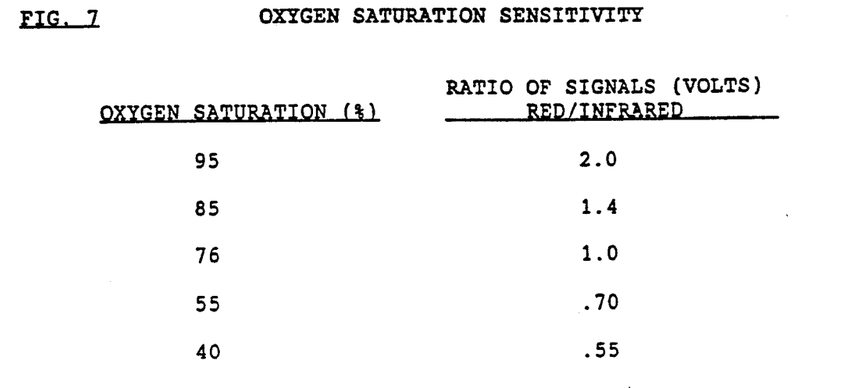
FIGS. 7-12 show various tables used in compensating the signals generated by the present invention for effects attributable to hematocrit, oxygen saturation, and pH.
Figure 8:
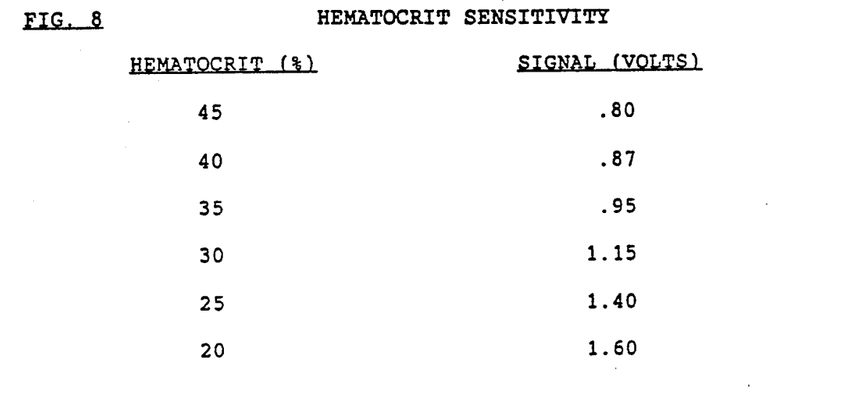
Figure 9:
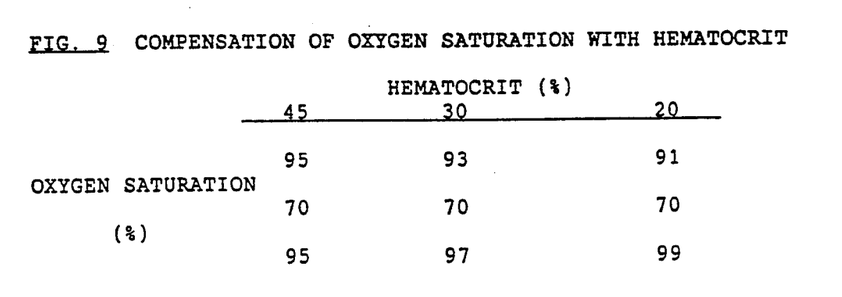
Figure 10:
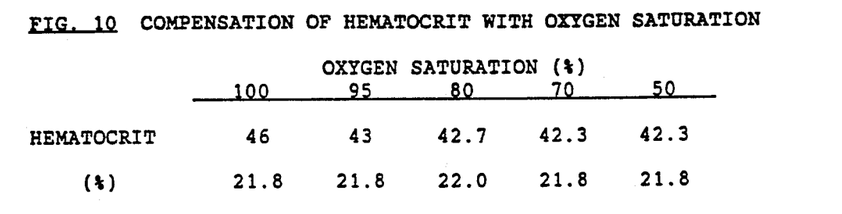
Figure 11:
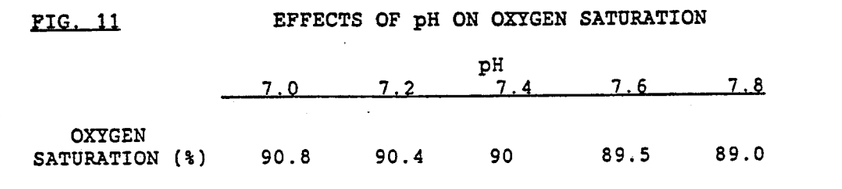
Figure 12:
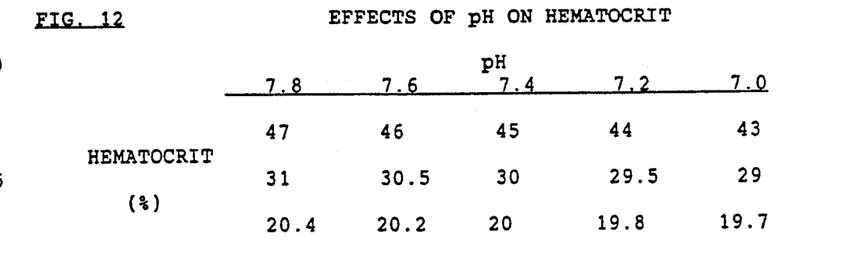

During operation of device 10, HCT1, after being compensated by HCT2, is used to obtain an uncompensated percentage of hematocrit in the blood. For example, as seen in FIG. 8 an HCT1 signal equal to 0.87 volts corresponds to an uncompensated blood hematocrit level of 40%. The ratio of SAT3/SAT1 is used to obtain an uncompensated percentage of oxygen saturation, after SAT1 has been compensated by SAT2 and SAT3 has been compensated by SAT4. For example, as seen in FIG. 7, a voltage ratio signal of 1.4 volts corresponds to an uncompensated oxygen saturation level of 85%. In compensating hematocrit for the effects of oxygen saturation, the hematocrit reading is normalized to an oxygen saturation level of 100%. For example, as seen in FIG. 10, an uncompensated hematocrit level of 42.7% obtained with an uncompensated oxygen saturation level of 80% corresponds to a compensated hematocrit level of 46%. In compensating oxygen saturation for the effects of hematocrit, the oxygen saturation reading is normalized to a hematocrit level of 45%. For example, as seen in FIG. 9, an uncompensated oxygen saturation level of 91% obtained with an uncompensated hematocrit level of 20% corresponds to a compensated oxygen saturation level of 95%. The compensated hematocrit and oxygen saturation levels are stored in memory module 53 of device 10. The compensated hematocrit level is further compensated for the effects of pH by normalizing the compensated hematocrit level to a pH of 7.4. For example, as seen in FIG. 12, a compensated hematocrit level of 29.5% at an inputted pH value of 7.2 corresponded to a normalized hematocrit level of 30%. The compensated oxygen saturation level is also further compensated for the effects of pH by normalizing the level to a pH of 7.4. For example, as seen in FIG. 11, a compensated oxygen saturation level of 39.5% at an inputted pH value of 7.6 corresponds to a normalized oxygen saturation level of 90%. The hematocrit level, after being normalized/compensated for the effects of oxygen saturation and pH is outputted on display panel 16 as is the oxygen saturation level after the normalization/compensation thereof for the effects of hematocrit and pH. As previously stated, the values included in the tables shown in FIGS. 7-12 are samplings included only for purposes of more clearly explaining the aforementioned sequence and are not intended to encompass the entire range of compensation values.

It will be appreciated that many alternatives of the signal processing system disclosed may be utilized and that the foregoing is intended only to illustrate one possible process which may be utilized in conjunction with such signals. Additionally, it will be recognized that the manipulative steps, i.e. sequence of events for controlling the CPU 56, motor 60, memory 58, and plural sensors, as well as the processing of signals received from the plural sensors, is stored in a program accessible by the CPU 56.

THE SYRINGE

Referring now to FIG. 2, syringe 8 is specifically adapted to be used in conjunction with device 10 of the present invention. Syringe 8 generally comprises tubular member 2 having a flange 3 disposed on one end thereof, with a needle 4 disposed on the opposing end. Flange 3 defines an opening therein adapted to receive piston 5. Disposed within a portion of tubular member 2 is a generally planar, rectangularly-shaped, longitudinally extending optical window 6. It will be understood that optical window 6 may have a plurality of geometric shapes, and that such rectangular shape is only one embodiment thereof. Window 6 is positioned on tubular member 2 such that when flange 3 is received into flange slot 25 formed in carriage 14, window 6 will be vertically aligned with fibers 28, 30, 32, 34, and 36, such that light from fiber 28 is emitted through window 6 into syringe 8 and reflected back through window 6 into fibers 30, 32, 34, and 36. Importantly, window 6 may be planar, concave, or convex on either or both its inner and outer surfaces. In the preferred embodiment of the present invention, window 6 has a concave configuration and is constructed from a transparent material, though device 10 is still operable if such material is diffuse. Though syringe 8 is utilized in conjunction with the preferred embodiment of the present invention, it will be appreciated that any syringe-like disposable vessel or cuvette may be utilized as a blood containing device for measurement operations in a static mode. Furthermore, any containment device open on either end and capable of handling blood in a flow-through mode may be utilized in conjunction with the device 10. It is also contemplated to use a protein-sensitive end cap 7 on syringe 8 to improve the accuracy of measuring device 10. Also included on a portion of syringe 8 is a piece of tape not shown) which can be used for cleaning the fiber optic surfaces, as previously set forth.

Importantly, the use of syringe 8 provides the advantage that once blood has been drawn therein, no further handling of the blood is required to obtain measurements of the hematocrit and oxygen saturation levels of the blood. In this respect, the risks associated with such blood handling attribuitable to AIDs and hepatitis are greatly diminished.

With the structure defined, the operation of the present invention may be described. In a static blood analysis environment, the syringe 8 is preferably utilized to obtain a blood sample from a patient in a conventional manner. A portion of the blood sample may subsequently be used to determine the pH of the blood sample, via conventional techniques, which pH value may subsequently be inserted into the memory 58 of the device with the operation of the keypad 18. Subsequently, the upper member 24 of the carriage may be closed, and a test or calibration switch 100 formed on the housing 12 may be manually depressed causing implementation of a test sequence to be initiated by the CPU 56. As previously described, in this test or calibration sequence, the LED's 42 and 44 are sequentially activated to emanate differing known wavelength light from fiber sensor 28 which is received by sensors 38 and 40. If the received signals generated by the optical sensors 38 and 40 are within predetermined differential values, the measurement operation may continue. Alternatively, if such differential are beyond predetermined values, an error message will be outputted by the CPU vis display 16. Such error message is indicative of the fact that the emitting fiber is inoperative or has become inoperative due to dirt accumulation at its distal end adjacent the recess 26 whereby the fiber 28 may be manually cleaned. Subsequent to cleaning, the calibration or test procedure may again be initiated to insure operation within system parameters and thereby insure measurement accuracy.

Following calibration, the syringe 8 containing the blood sample therewithin, may be positioned within the recess 26 formed within the cradle 14, whereby the window 6 is disposed above the plural optical sensors 36, 32, 28, 30, and 34. Subsequently, the upper member 24 of the cradle 14 may be disposed in its closed orientation and a measurement procedure via the device 10 may be initiated by manual depression of a measurement switch 102 formed on the housing 16. Manual depression of the measurement switch 102 causes the CPU to initiate a sequence of events wherein known wavelength light is sequentially emitted from the LED's 42 and 44 via optical fiber 28 and measured via plural sensors 30 and 32, and 34 and 36, in a manner previously described. The signal values obtained from the sensors 30, 32, 34, and 36 are then processed via the CPU 56 and compared to the published tables stored in memory 58. Such tables are derived from empirical results which compensate for hematocrit and blood saturation values based upon the relative values of such blood saturation and hematocrit values as well as pH values of the blood sample. Subsequently, the hematocrit value is output by the CPU via display 16. Subsequently, by manual depression of an oxygen saturation switch 104 formed on the housing 12, the CPU is directed to output the blood oxygen saturation value via display 16 to a user. As such, it will be recognized that the present invention provides a reliable, rapid, and economical means of providing an oxygen saturation value and hematocrit value of a blood sample to a user in a static blood sample environment.

Alternatively, the present invention is specifically adapted to provide a similar measurement of hematocrit and oxygen saturation in a flow-through blood environment. In such applications, the syringe 8 is replaced by a cuvette, opposite ends of which are attached in a blood circulation system attached to a patient. In such flow-through application environments, the motor 60 will be inactivated since the flow-through embodiment efficiently agitates the blood to avoid protein drop-out in the blood sample traveling through the cuvette. The sequence of events and operations of the measurement process, however, are the same as described supra in relation to static measurement environment.

Additional modifications and improvements of the invention may also be apparent to those skilled in the art, thus, the particular combination of parts described and illustrated herein is intended to represent only one embodiment of the invention, and is not intended to serve as limitations of alternative devices within the spirit and scope of the invention.

What is claimed is:

1. A syringe comprising:
   an elongate, tubular member having a proximal end, a distal end, and a hollow lumen extending longitudinally therethrough;
   a needle disposed on said proximal end of said tubular member, said needle being in fluid communication with said lumen;
   a flange formed on the distal end of said tubular member;
   a piston insertable through said flange into the distal end of said tubular member, said piston being reciprocally movable within said lumen; and
   a single optical window member having inner and outer surfaces, said window member being insert into said tubular member in a manner wherein said inner surface defines a portion of the lumen, and constructed of a material which provides a substantially transparent, repeatable optical light path from the exterior of the tubular member to the lumen.

2. The syringe of claim 1 wherein said window member has a rectangularly shaped configuration.

3. The syringe of claim 2 wherein said inner and outer surfaces have generally planar configurations.

4. The syringe of claim 2 wherein said outer surface has a convex configuration and said inner surface has a concave configuration.

5. The syringe of claim 2 wherein said outer surface has a concave configuration and said inner surface has a convex configuration.

6. The syringe of claim 2 wherein said outer surface has a convex configuration and said inner surface has a planar configuration.

7. The syringe of claim 2 wherein said outer surface has a concave configuration and said inner surface has a planar configuration.

8. The syringe of claim 2 wherein said inner and outer surfaces have concave configurations.

9. The syringe of claim 2 wherein said inner and outer surfaces have convex configurations.

10. The syringe of claims 1 further comprising an end cap selectively positionable over said needle.

* * * * *